(12) United States Patent
Yu (10) Patent No.: US 12,196,738 B2
(45) Date of Patent: Jan. 14, 2025

(54) SOIL TESTING DEVICE

(71) Applicant: Jian Yu, Shenzhen (CN)

(72) Inventor: Jian Yu, Shenzhen (CN)

(*) Notice: Subject to any disclaimer, the term of this patent is extended or adjusted under 35 U.S.C. 154(b) by 235 days.

(21) Appl. No.: 17/887,502

(22) Filed: Aug. 14, 2022

(65) Prior Publication Data

US 2024/0053320 A1   Feb. 15, 2024

(51) Int. Cl.
*G01N 33/24* (2006.01)
*A01G 2/00* (2018.01)
*A01G 25/16* (2006.01)
*A01G 27/00* (2006.01)
*G01N 27/02* (2006.01)
*G01N 27/04* (2006.01)
*G01N 27/12* (2006.01)

(52) U.S. Cl.
CPC .......... *G01N 33/24* (2013.01); *G01N 27/025* (2013.01); *G01N 27/048* (2013.01); *G01N 27/121* (2013.01); *G01N 33/246* (2013.01); *A01G 2/00* (2018.02); *A01G 25/167* (2013.01); *A01G 27/005* (2013.01); *G01N 33/245* (2024.05)

(58) Field of Classification Search
CPC .. G01N 27/121; G01N 27/246; G01N 33/245; G01N 33/246; A01G 25/167
USPC ........................................................ 324/696
See application file for complete search history.

(56) References Cited

U.S. PATENT DOCUMENTS

| | | | | |
|---|---|---|---|---|
| 2,970,267 A | * | 1/1961 | Pfeffer | G01R 5/14 |
| | | | | 324/156 |
| 3,189,935 A | * | 6/1965 | Euga | H01J 5/08 |
| | | | | 15/104.04 |
| 4,052,667 A | * | 10/1977 | Schwartz | G01N 27/048 |
| | | | | 324/696 |
| 2023/0200317 A1 | * | 6/2023 | De | G06N 3/0464 |
| | | | | 702/127 |

OTHER PUBLICATIONS

Hareendran, TK; "Soil Meter"; Web page <https://www.electroschematics.com/soil-meter/>; Oct. 20, 2021; 7 pages (Year: 2021).*
Ray ("Reverse Engineer a Cheap Wireless Soil Moisture Sensor"; Web page <https://rayshobby.net/wordpress/reverse-engineer-a-cheap-wireless-soil-moisture-sensor/>; Pub. Date Aug. 17, 2020; retrieved from Internet Wayback Machine (Year: 2020).*

* cited by examiner

*Primary Examiner* — Eman A Alkafawi
*Assistant Examiner* — Rahul Maini (57) ABSTRACT

A soil testing device includes at least one sensor assembly, after the sensor assembly is inserted into soil, the sensor assembly and the soil cooperatively form a battery cell; and an analog meter, electrically connected with the at least one sensor assembly, the at least one sensor assembly is configured to transmit a micro current of the battery cell reflecting a measure of soil characteristic to the analog meter, the analog meter is configured to display a value reflecting the soil characteristic.

18 Claims, 8 Drawing Sheets

SOIL TESTING DEVICE

FIELD

This disclosure relates to a technical field of electronic gardening tools, specifically to a soil testing device.

BACKGROUND

Fertility, moisture and pH meters on the consumer market use analog or digital meters to display the fertility, moisture and pH value of soil. The analog meters may require expensive manual calibration that has to be done at the factory. On the other hand, the digital meters require extra calibration circuitry that also need manual calibration before taking the measure in the soil.

Therefore, there is presently a need for an improved soil testing device that can be manufactured in a cost-effective manner and address the foregoing issues.

SUMMARY

The present disclosure provides a soil testing device, the soil testing device has the advantages of convenient, low cost, and multi-function.

To achieve the above purpose, the present disclosure provides a soil testing device, which includes at least one sensor assembly, after the sensor assembly is inserted into soil, the sensor assembly and the soil cooperatively form a battery cell; and an analog meter, electrically connected with the at least one sensor assembly, the sensor assembly is configured to transmit a micro current of the battery cell reflecting a measure of soil characteristic to the analog meter, the analog meter is configured to display a value reflecting the soil characteristic.

In at least one embodiment, the soil testing device further includes: at least one sleeve, detachably sleeved on the at least one sensor assembly and configured to burnish the at least one sensor assembly.

In at least one embodiment, the sensor assembly includes: a sensor; and a sensor probe, connected with the sensor, after the sensor is inserted into the soil, the sensor, the sensor probe, and the soil cooperatively form the battery cell.

In at least one embodiment, the sensor assembly is a pH meter, a moisture meter, or a fertility meter.

In at least one embodiment, the analog meter includes: a first negative pole, electrically connected with the at least one sensor assembly.

In at least one embodiment, the soil testing device according to claim further includes: a switching assembly, configured to electrically connect the analog meter with the sensor assembly, or configured to isolate the analog meter from the sensor assembly.

In at least one embodiment, the analog meter further includes: a first positive pole; and the switching assembly includes: a printed circuit board; and a first connecting position, arranged on the printed circuit board and electrically connected with the first positive pole.

In at least one embodiment, the switching assembly further includes: at least one second connecting position, arranged on the printed circuit board and electrically connected with the at least one sensor assembly.

In at least one embodiment, the soil testing device further includes: a photosensitive sensor, connected with the analog meter and the switching assembly, the switching assembly is configured to electrically connect the analog meter with the photosensitive sensor, or configured to isolate the analog meter from the photosensitive sensor.

In at least one embodiment, the photosensitive sensor includes: a second positive pole, connected with the analog meter; and a second negative pole, connected with the switching assembly.

In at least one embodiment, the switching assembly further includes: a third connecting position, connected with the second negative pole of the photosensitive sensor.

In at least one embodiment, the switching assembly further includes: an actuating element, connected with the printed circuit board, the actuating element is configured to electrically connect the analog meter with the sensor assembly, or configured to isolate the analog meter from the sensor assembly.

In at least one embodiment, the switching assembly further includes: an actuating element, connected with the printed circuit board, the actuating element is configured to electrically connect the analog meter with the photosensitive sensor, or configured to isolate the analog meter from the photosensitive sensor.

In at least one embodiment, the soil testing device further includes: a housing, the housing defines a window; and the analog meter is received in the housing, and the analog meter further includes: a dial, having at least one data range; and a pointer, movably arranged on the dial and configured to display the value reflecting the soil characteristic within the data range, the dial and pointer are at least partially exposed from the window.

In at least one embodiment, the analog meter further includes: a rotating element, connected with the pointer; a metal coil, wound around the rotating element and electrically connected with the at least one sensor assembly; and a magnetic element, the metal coil is arranged in a magnetic field of the magnetic element, after the metal coil is energized by the micro current, the metal coil is configured to drive the rotating element and the pointer to rotate under an action of a magnetic force of the magnetic element.

In at least one embodiment, the soil testing device further includes: a housing, the housing defines a first through hole; and the sensor probe defines: a second through hole communicated with the first through hole, the first through hole and the second through hole are configured to receive an electric wire for electrically connect the at least one sensor assembly with the analog meter.

In at least one embodiment, the soil testing device further includes: a connecting element, configured to connect the at least one sensor assembly with the housing.

In at least one embodiment, the connecting element includes: at lease one receiving groove, communicated with the first through hole and the second through hole, the sensor assembly is received in the receiving groove and the first through hole.

In at least one embodiment, the housing further includes: at least one clamping portion; and the connecting element further includes: at least one clamping groove, the clamping portion is clamped in the clamping groove.

In at least one embodiment, the soil testing device further includes: a housing, the housing defines a third through hole; and the photosensitive sensor further includes: a sensor body, received in the third through hole.

In the technical solution of the present disclosure, the soil testing device includes an least one sensor assembly and an analog meter electrically connected with the sensor assembly, after the sensor assembly is inserted into soil, the sensor assembly 10 and the soil cooperatively form a battery cell, the sensor assembly transmits a micro current of the battery cell reflecting a measure of soil characteristic to the analog meter, the analog meter displays a value reflecting the soil characteristic. In this way, the soil characteristic, such as, the pH value, the moisture value, and the fertility value, can be displayed on the analog meter without extra calibration. Therefore, the soil testing device of the present disclosure has the advantages of convenient, low cost, and multi-function.

BRIEF DESCRIPTION OF THE DRAWINGS

Implementations of the present disclosure will now be described, by way of embodiment, with reference to the attached FIG.s. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION

It will be appreciated that for simplicity and clarity of illustration, where appropriate, reference numerals have been repeated among the different FIG.s to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. the present disclosure is illustrated by way of example and not by way of limitation in the FIG.s of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the application, "a plurality of" means two or more, unless otherwise specifically defined.

Please referring to FIGS. 1 to 9, the present disclosure provides a soil testing device 100 according to an embodiment.

Figure 1:
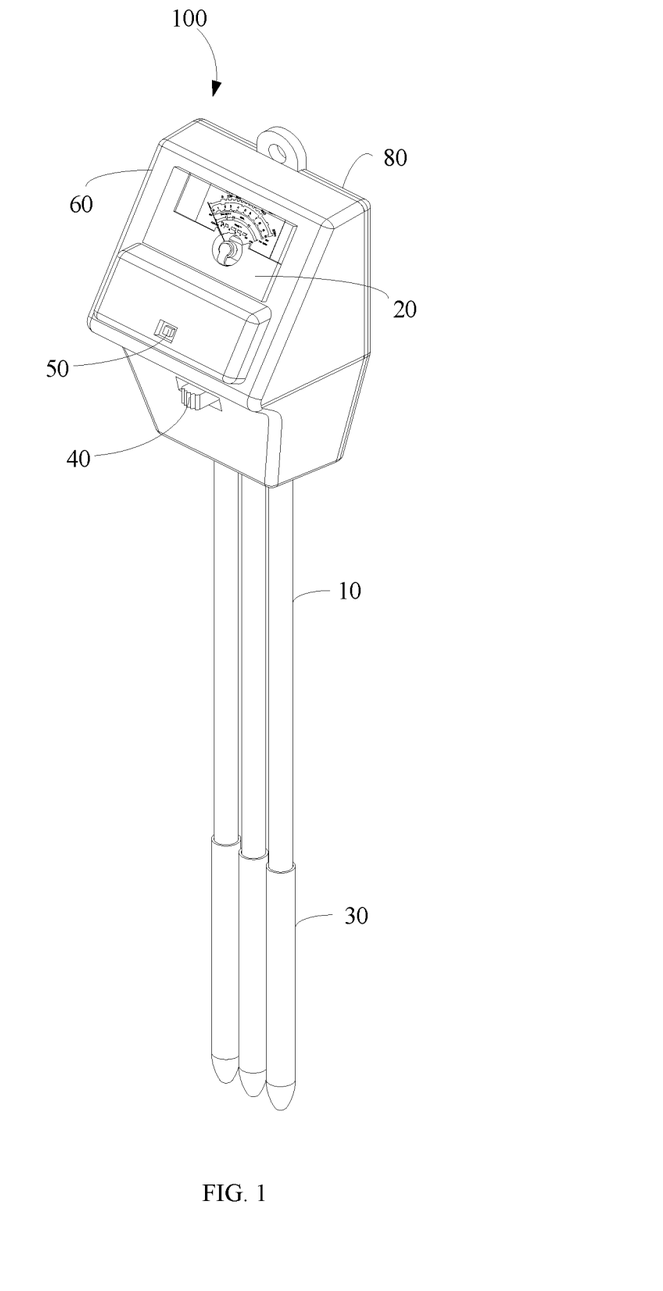
FIG. 1 is a structure diagram of a soil testing device according to an embodiment of the present disclosure.
Figure 9:
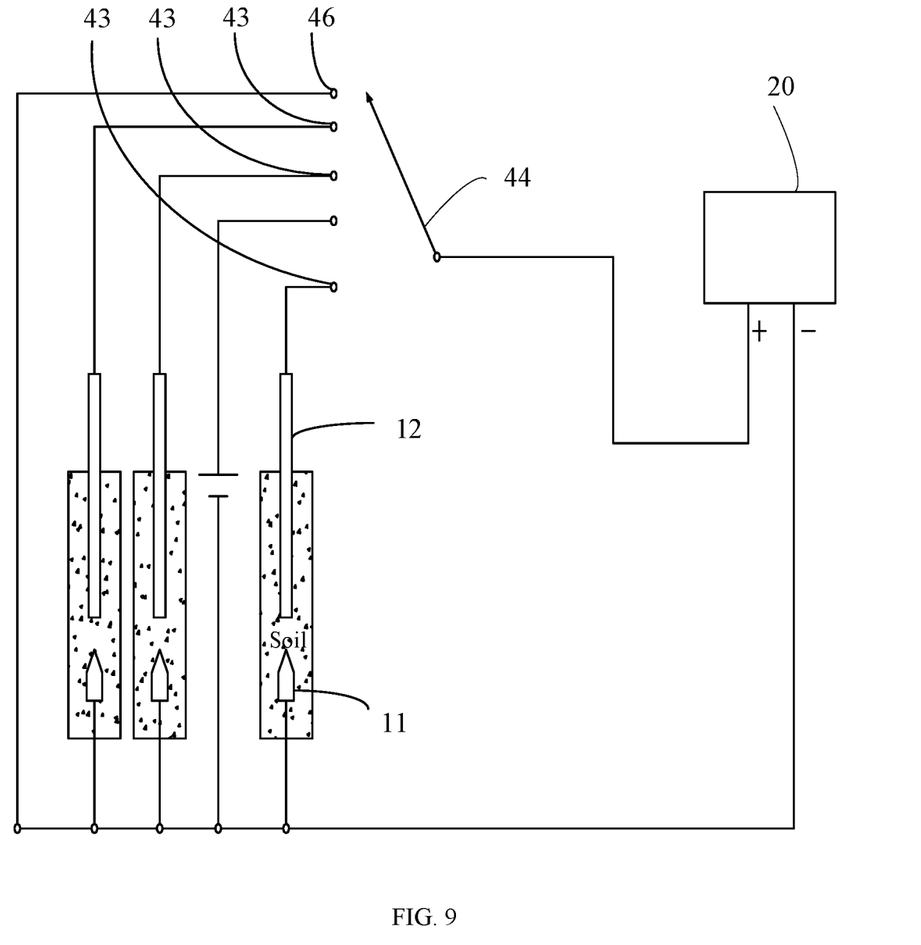
FIG. 9 is a block diagram of the soil testing device of FIG. 1.

The soil testing device 100 includes at least one sensor assembly 10 and an analog meter 20 electrically connected with the at least one sensor assembly 10. After the sensor assembly 10 is inserted into soil, the sensor assembly 10 and the soil cooperatively form a battery cell, the sensor assembly 10 is configured to transmit a micro current of the battery cell reflecting a measure of soil characteristic to the analog meter 20, and thereby the analog meter 20 is configured to display a value reflecting the soil characteristic.

Figure 2:
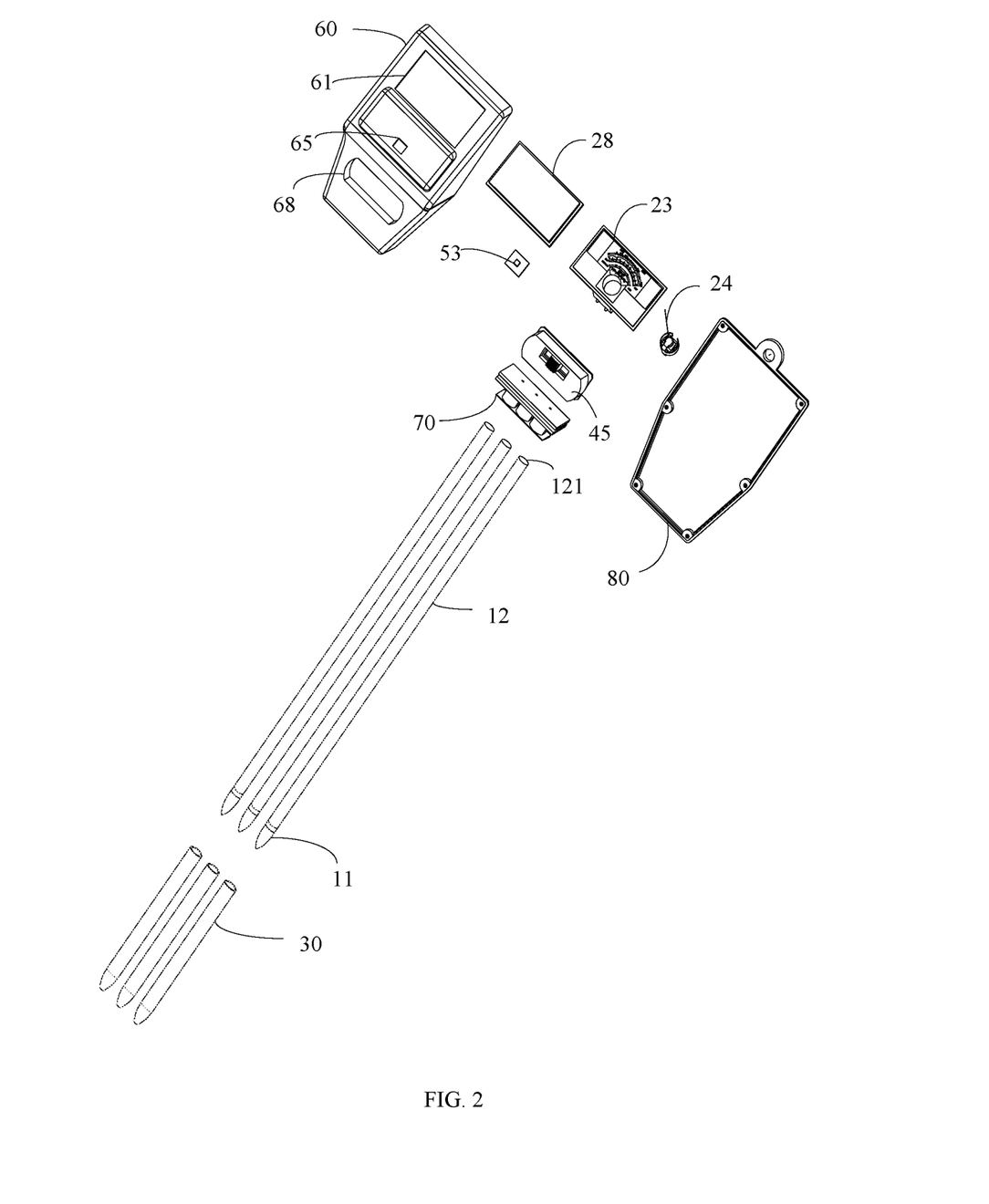
FIG. 2 is an exploded diagram of the soil testing device of FIG. 1.
Figure 3:
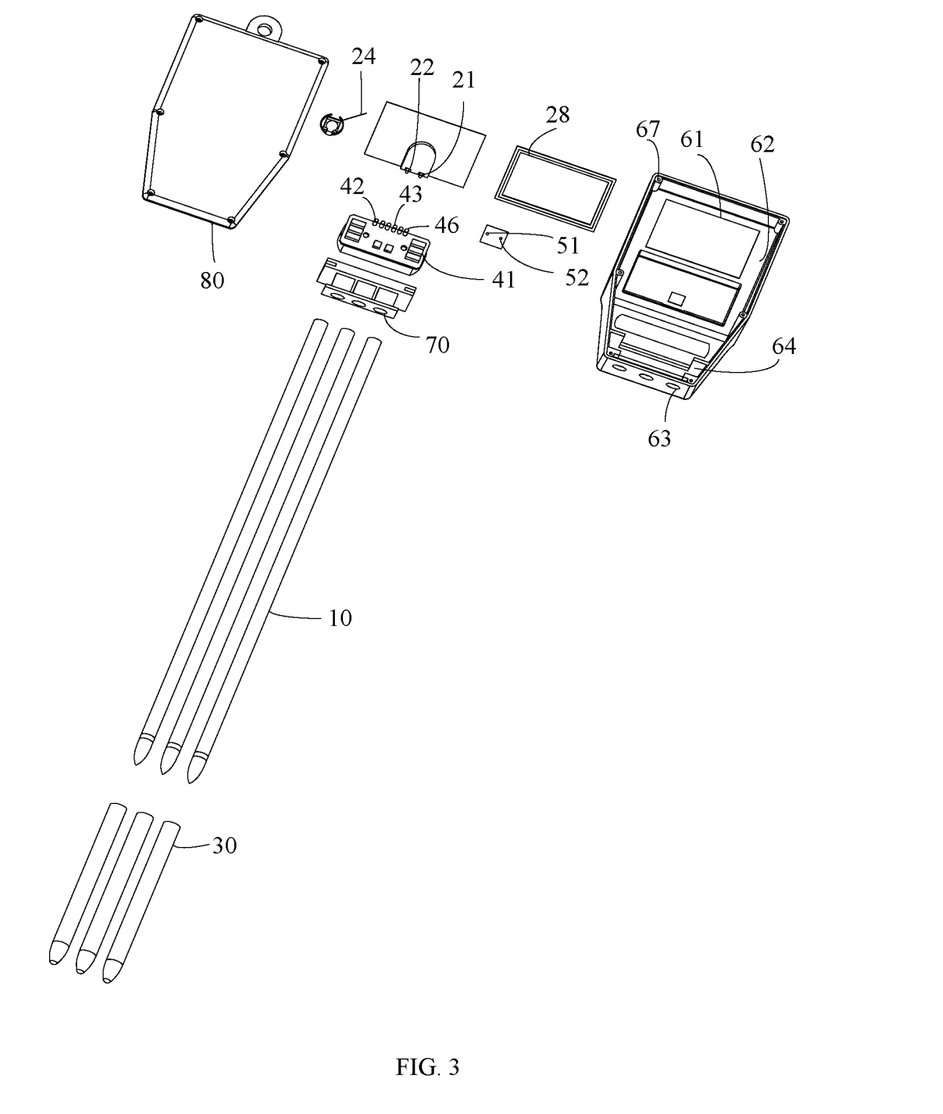
FIG. 3 is similar to FIG. 2, but shown from another view.

In at least one embodiment, the sensor assembly 10 includes a sensor 11 and a sensor probe 12 connected with the sensor 11. After the sensor 11 is inserted into the soil, the sensor 11, the sensor probe 12, and the soil cooperatively form the battery cell. It should be understood that, the sensor 11 is capable of generating a varying current in accordance with a level of pH/moisture/fertility sensed at the sensor 11.

In at least one embodiment, the sensor 11 is made of metal, such as, aluminum, aluminium alloy, copper, copper alloy, or the like. As the sensor 11 is made of metal, the sensor 11 may be easily oxidized to form an oxide layer on an outer surface of the sensor 11, the oxide layer may affect the accuracy of the sensor assembly 10.

In at least one embodiment, the sensor probe 12 is made of metal, such as, aluminum, aluminium alloy, copper, copper alloy, or the like.

In at least one embodiment, the sensor assembly 10 can be a pH meter adapted to measure a pH value of the soil, a moisture meter adapted to measure a moisture value of the soil, or a fertility meter adapted to measure a fertility value of the soil. In detail, the pH meter has a pH sensor and a pH sensor probe; the moisture meter has a moisture sensor and a moisture sensor probe; the fertility meter has a fertility sensor and a fertility sensor probe.

In at least one embodiment, the soil testing device 100 includes three sensor assemblies 10 including the pH meter, the moisture meter, and the fertility meter.

In the technical solution of the present disclosure, the soil testing device 100 includes an least one sensor assembly 10 and an analog meter 20 electrically connected with the sensor assembly 10. After the sensor assembly 10 is inserted into soil, the sensor assembly 10 and the soil cooperatively form a battery cell, the sensor assembly 10 transmits a micro current of the battery cell reflecting a measure of soil characteristic to the analog meter 20, and the analog meter 20 displays a value reflecting the soil characteristic. In this way, the soil characteristic, such as, the pH value, the moisture value, or the fertility value, can be displayed on the analog meter 20 without extra calibration. Therefore, the soil testing device 100 of the present disclosure has the advantages of convenient, low cost, and multi-function.

The soil testing device 100 further includes at least one sleeve 30 detachably sleeved on the at least one sensor assembly 10 and configured to burnish the at least one sensor assembly 10.

In at least one embodiment, a length of the sleeve 30 is no less than that of the sensor 11.

In at least one embodiment, an inner surface of the sleeve 30 may be a frosting surface, or has a thread structure 31, such as, protrusions, or the like. So that, user can use the sleeve 30 to polish the sensor 11 and at least partly remove the oxide layer on the sensor 11.

In the technical solution of the present disclosure, the soil testing device 100 further includes at least one sleeve 30, user can use the sleeve 30 to burnish the sensor 11, to remove the oxide layer on the sensor 11, further to ensure the accuracy of the sensor assembly 10.

Figure 6:
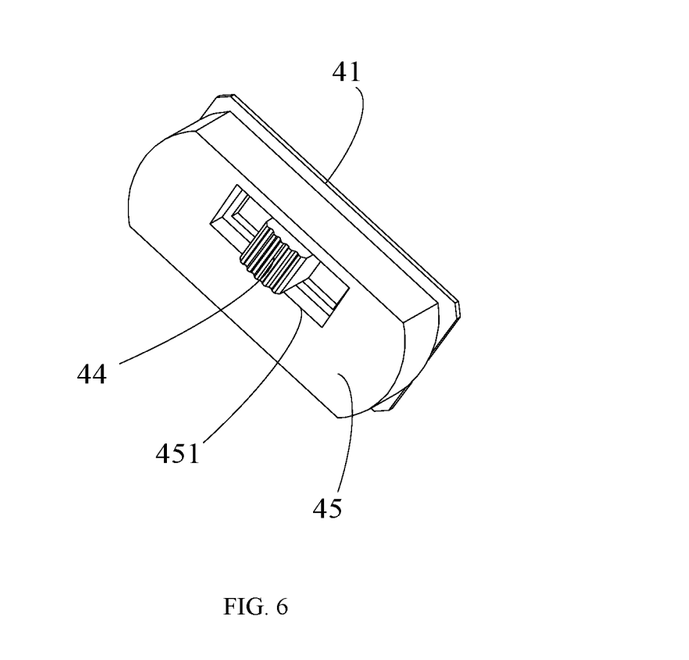
FIG. 6 is a structure diagram of a switching assembly of the soil testing device of FIG. 2.

The soil testing device 100 further includes a switching assembly 40, the switching assembly 40 is configured to electrically connect the analog meter 20 with the sensor assembly 10, or configured to isolate the analog meter 20 from the sensor assembly 10. The analog meter 20 includes a first negative pole 21 electrically connected with the at least one sensor assembly 10, and a first positive pole 22 electrically connected with the switching assembly 40.

In at least one embodiment, the switching assembly 40 includes a printed circuit board 41, a first connecting position 42 arranged on the printed circuit board 41 and electrically connected with the first positive pole 22 of the analog meter 20, at least one second connecting position 43 arranged on the printed circuit board 41 and electrically connected with the at least one sensor assembly 10, an actuating element 44 connected with the printed circuit board 41, and a supporting element 45 configured to support the printed circuit board 41 and the actuating element 44. The actuating element 44 may be an actuator configured to electrically connect the analog meter 20 with the sensor assembly 10, or configured to isolate the analog meter 20 from the sensor assembly 10.

In at least one embodiment, the switching assembly 40 may be a toggle switch or a slide switch which is common in the art, so there is no need to detailedly describe structures of the toggle switch or the slide switch. It should be understood that, the switching assembly 40 further includes other essential elements, such as, spring, circular bead, and so on.

In at least one embodiment, a quantity of the second connecting position 43 is equal to a quantity of the sensor assembly 10.

In at least one embodiment, the second connecting position 43 is electrically connected with the sensor probe 12 through a metal wire (not shown). An end of the metal wire may be connected with an inner surface of a second through hole 121 of the probe 12, another end of the metal wire may be connected with the second connecting position 43.

In at least one embodiment, the supporting element 45 may be made of insulation materials.

In at least one embodiment, the supporting element 45 defines an accommodating groove 451, the actuating element 44 is partially received in the accommodating groove 451. The printed circuit board 41 covers an end of the accommodating groove 451 away from the actuating element 41. User can move the actuating element 44 on the printed circuit board 41 to turn on or turn off a circuit composed of the analog meter 20 and the sensor assembly 10. In this way, the actuating element 44 can be configured to electrically connect the analog meter 20 with the sensor assembly 10, or configured to isolate the analog meter 20 from the sensor assembly 10.

In the technical solution of the present disclosure, the soil testing device 100 further includes a switching assembly 40, the switching assembly 40 is configured to electrically connect the analog meter 20 with the sensor assembly 10, or configured to isolate the analog meter 20 from the sensor assembly 10. In this way, the soil testing device 100 can test the pH value, the moisture value, or the fertility value of the soil.

The soil testing device 100 further includes a photosensitive sensor 50 connected with the analog meter 20 and the switching assembly 40, the switching assembly 40 is configured to electrically connect the analog meter 20 with the photosensitive sensor 50, or configured to isolate the analog meter 20 from the photosensitive sensor 50.

In at least one embodiment, the photosensitive sensor 50 includes a second positive pole 51 connected with the analog meter 20, and a second negative pole 52 connected with the switching assembly 40.

In at least one embodiment, the second positive pole 51 of the photosensitive sensor 50 is electrically connected with the first negative pole 21 of the analog meter 20.

In at least one embodiment, the switching assembly 40 further includes a third connecting position 46 arranged on the printed circuit board 41 and connected with the second negative pole 52 of the photosensitive sensor 50. The actuating element 44 is configured to electrically connect the analog meter 20 with the photosensitive sensor 50, or configured to isolate the analog meter 20 from the photosensitive sensor 50.

In at least one embodiment, the third connecting position 46 is separated from the first connecting position 42 and the second connecting position 43.

In the technical solution of the present disclosure, the soil testing device 100 further includes a photosensitive sensor 50 connected with the analog meter 20 and the switching assembly 40, the photosensitive sensor 50 can convert a light signal into an electrical signal, after the current generated by the photosensitive sensor 50 is transmitted to the analog meter 20, the analog meter 20 can display the luminance value. It should be understood that, the greater the current, the larger the luminance value.

Figure 8:
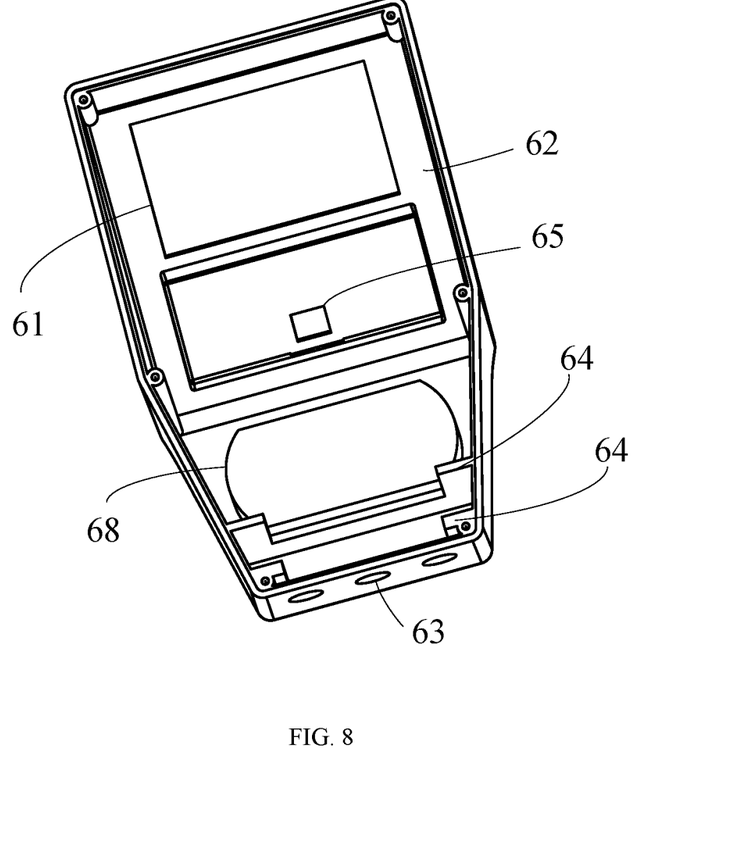
FIG. 8 is a structure diagram of a housing of the soil testing device of FIG. 2.

The soil testing device 100 further includes a housing 60, the housing 60 defines a window 61 and a receiving cavity 62 communicated with the window 61, the analog meter 20, the switch assembly 40, the photosensitive sensor 50 are received in the receiving cavity 62 of the housing 60.

Figure 4:
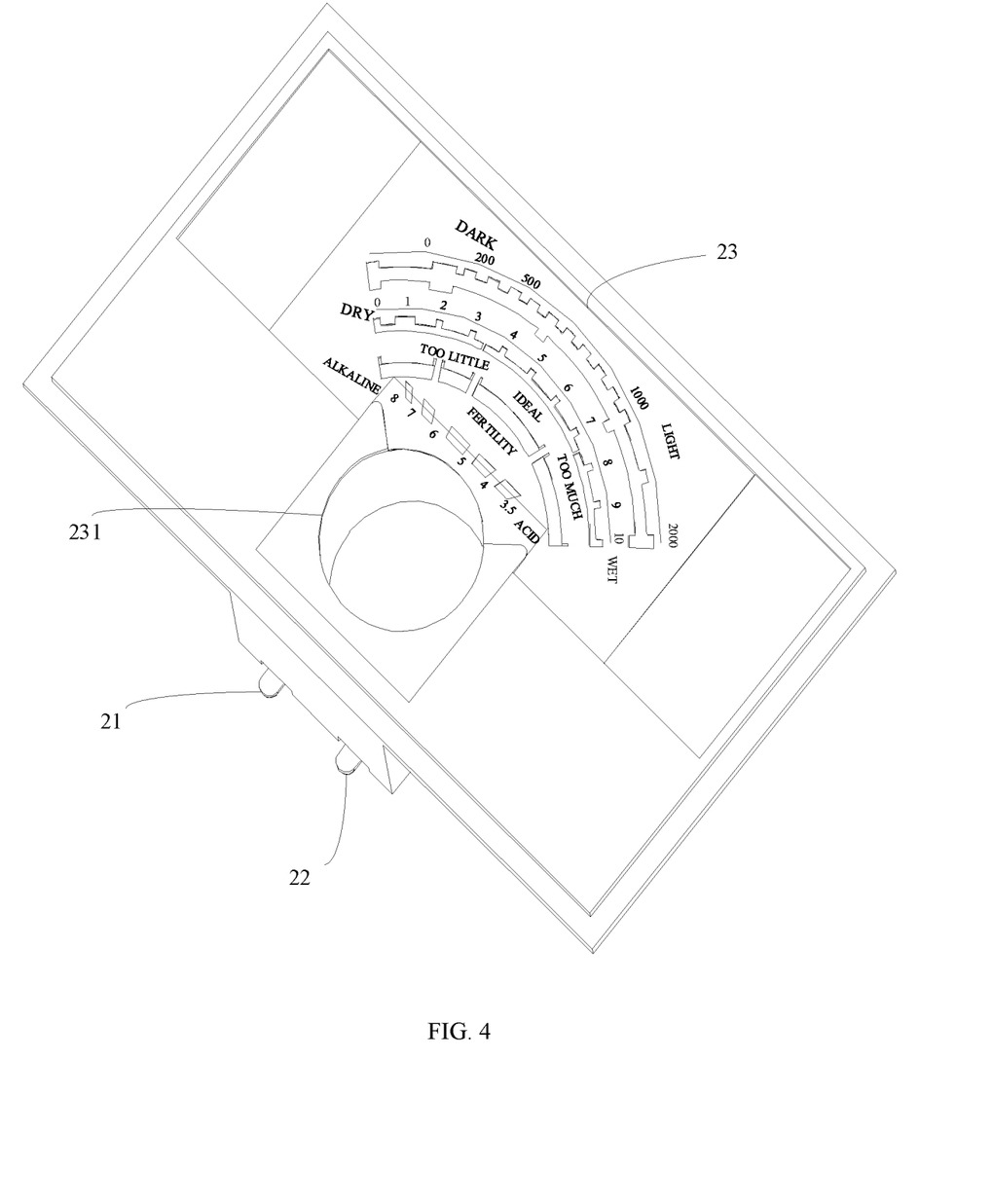
FIG. 4 is a structure diagram of a dial of the soil testing device of FIG. 2.

In at least one embodiment, the analog meter 20 further includes a dial 23 having at least one data range, and a pointer 24 movably arranged on the dial 23 and configured to display the value reflecting the soil characteristic within the data range, the dial 23 and pointer 24 are at least partially exposed from the window 61.

In at least one embodiment, the data range includes a pH value date range, a moisture value date range, a fertility value date range, and a luminance value date range.

Figure 7:
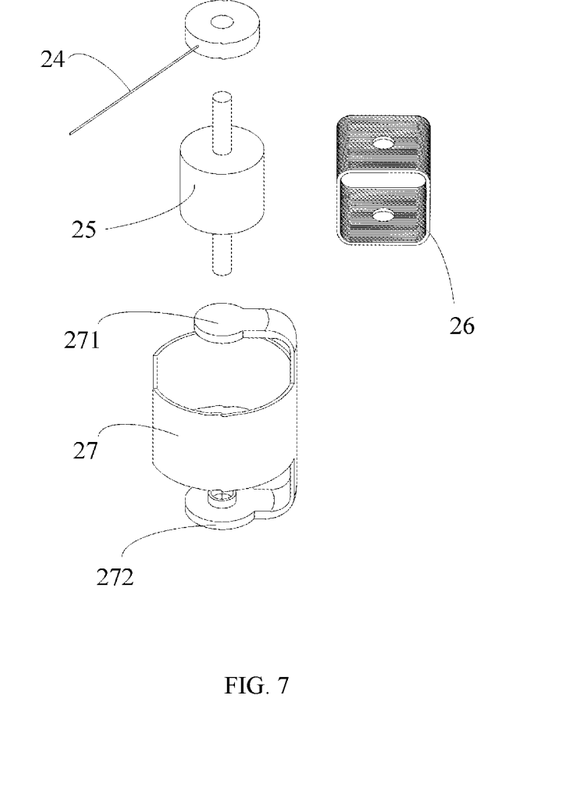
FIG. 7 is an exploded diagram of a pointer, a rotating element, a metal coil, and a magnetic element of the soil testing device of FIG. 2.

In at least one embodiment, the analog meter 20 further includes a rotating element 25 connected with the pointer 24, a metal coil 26 wound around the rotating element 25 and electrically connected with the at least one sensor assembly 10, and a magnetic element 27, the metal coil 26 is arranged in a magnetic field of the magnetic element 27, after the metal coil 26 is energized by the micro current, the metal coil 26 is configured to drive the rotating element 25 and the pointer 24 to rotate under an action of a magnetic force of the magnetic element 27.

In at least one embodiment, the dial 23 defines a receiving hole 231, the pointer 24, the rotating element 25, the metal coil 26, and the magnetic element 27 are received in the receiving hole 231.

In at least one embodiment, the metal coil 26 is made of copper.

In at least one embodiment, the magnetic element 27 is substantially U-shape, and the metal coil 26 is received in the U-shaped magnetic element 27. So that, the magnetic field generated by the magnetic element 27 can affect the metal coil 26 received in the U-shaped magnetic element 27 and drive the metal coil 26, the rotating element 25, and the pointer 24 to rotate.

In at least one embodiment, the magnetic element 27 includes a first connecting end 271 and a second connecting end 272 spaced apart from the first connecting end 271, the rotating element 25 is arranged between the first connecting end 271 and the second connecting end 272. Preferably, the rotating element 25 is rotatably connected with the first connecting end 271 and the second connecting end 272. An end of the metal coil 26 is electrically connected with the first negative pole 21. The pointer 24 is arranged on the rotating element 25. So that the current generated by the sensor assembly 10 can be transmitted to the metal coil 26, and the energized metal coil 26 can rotate under the magnetic force of the magnetic element 27, and drives the pointer 24 and the rotating element 25 to rotate.

In at least one embodiment, the first connecting end 271 and the second connecting end 272 are spaced apart from each other and extended towards a same direction.

In at least one embodiment, the analog meter 20 further includes a transparent cover 28, the transparent cover 28 is configured to cover the dial 23 and exposed from the window 61.

In at least one embodiment, the housing 60 defines a first through hole 63, an electric wire may pass through the first through hole 63 and the second through hole 121 and electrically connect the at least one sensor assembly 10 with the analog meter 20.

In at least one embodiment, a quantity of the electric wire is more than one, and the pH sensor, the moisture sensor, and the fertility sensor can be connected with the first negative pole 21 of the analog meter 20 by the electric wires.

In at least one embodiment, the second positive pole 51 of the photosensitive sensor 50 can be connected with the first negative pole 21 of the analog meter 20 by another electric wire (not shown), and the second negative pole 52 of the photosensitive sensor 50 can be connected the third connecting position 46 of the switch assembly 40 by a further electric wire.

In at least one embodiment, when the pH sensor probe 12 is inserted into the soil and the actuating element 44 switches to a pH testing position, the pH sensor 11, the soil, the pH sensor probe 12 and the analog meter 20 are in series connection with each other. The pH sensor 11, the soil, and the pH sensor probe 12 cooperatively form a first battery cell, which can generate a first micro current which can be transmitted to the analog meter 20. That is, a first circuit composed of the soil, the pH sensor 11, the pH sensor probe 12, and the analog meter 20 is formed, and the first micro current can be transmitted to the analog meter 20. After the first micro current is transmitted to the analog meter 20, the rotating element 25 rotates to drive the pointer 24 to move over a scale on the pH data range of the analog meter 20, so user can readout the pH value of the soil.

In at least one embodiment, when the moisture sensor probe 12 is inserted into the soil and the actuating element 44 switches to a moisture testing position, the moisture sensor 11, the soil, the moisture sensor probe 12 and the analog meter 20 are in series connection with each other. The moisture sensor 11, the soil, and the moisture sensor probe 12 cooperatively form a second battery cell, which can generate a second micro current which can be transmitted to the analog meter 20. That is, a second circuit composed of the soil, the moisture sensor 11, the moisture sensor probe 12, and the analog meter 20 is formed, and the second micro current can be transmitted to the analog meter 20. After the second micro current is transmitted to the analog meter 20, the rotating element 25 rotates to drive the pointer 24 to move over a scale on the moisture data range of the analog meter 20, so user can readout the moisture value of the soil.

In at least one embodiment, when the fertility sensor probe 12 is inserted into the soil and the actuating element 44 switches to a fertility testing position, the fertility sensor 11, the soil, the fertility sensor probe 12 and the analog meter 20 are in series connection with each other. The fertility sensor 11, the soil, and the fertility sensor probe 12 cooperatively form a third battery cell, which can generate a third micro current which can be transmitted to the analog meter 20. That is, a third circuit composed of the soil, the fertility sensor 11, the fertility sensor probe 12, and the analog meter 20 is formed, and the third micro current can be transmitted to the analog meter 20. After the third micro current is transmitted to the analog meter 20, the rotating element 25 rotates to drive the pointer 24 to move over a scale on the fertility data range of the analog meter 20, so user can readout the fertility value of the soil.

In at least one embodiment, when the actuating element 44 switches to a luminance testing position, the photosensitive sensor 50 are connected with the analog meter 20. The photosensitive sensor 50 can convert the light signal into the electrical signal and transmit the electrical signal to the analog meter 20. That is, a fourth circuit composed of the photosensitive sensor 50 and the analog meter 20 is formed, and a fourth micro current can be transmitted to the analog meter 20. After the fourth micro current is transmitted to the analog meter 20, the rotating element 25 rotates to drive the pointer 24 to move over a scale on the luminance data range of the analog meter 20, so user can readout the luminance value.

In at least one embodiment, the housing 60 defines a third through hole 65, the photosensitive sensor 50 further includes a sensor body 53 received in the third through hole 65. The sensor body 53 is configured to convert the light signal into the electrical signal and transmit the electrical signal to the analog meter 20.

In at least one embodiment, the housing 60 defines a fourth through hole 68 communicated with the receiving cavity 62, the actuating element 44 can be exposed from the fourth through hole 68.

Figure 5:
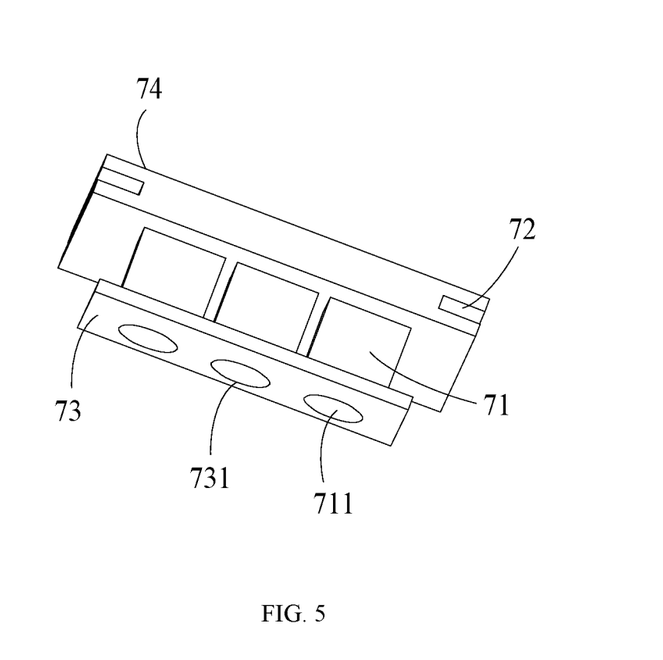
FIG. 5 is a structure diagram of a connecting element of the soil testing device of FIG. 2.

The soil testing device 100 further includes a connecting element 70, which is configured to connect the at least one sensor assembly 10 with the housing 60.

In at least one embodiment, the connecting element 70 includes at least one receiving portion 71 received in the receiving cavity 62, a quantity of the receiving portion 71 is equal to a quantity of the sensor assembly 10. The receiving portion 71 defines a receiving groove 711 communicated with the receiving cavity 62, the sensor probe 12 of the sensor assembly 10 is passed through the first through hole 63 and received in the receiving groove 711. So that, the sensor assembly 10 can be connected with the housing 60.

In at least one embodiment, the receiving groove 711 passes through two opposite sides of the receiving portion 71, so that the receiving groove 711 can communicate with the receiving cavity 62, the sensor probe 12 of the sensor assembly 10 can receive in the receiving groove 711, and the electric wires can pass through the first through hole 63 and the receiving groove 711 to connect with the first negative pole 21 of the analog meter 20.

In at least one embodiment, the housing 60 further includes at least one clamping portion 64, the connecting element 70 further includes at least one clamping groove 72, the clamping portion 64 is clamped in the clamping groove 72.

In at least one embodiment, the clamping portion 64 is a clamping plate protruded from an inner surface of the housing 60.

In at least one embodiment, the housing 60 includes an least one first connecting column 67, the first connecting column 67 defines a receiving hole (not labeled). The soil testing device 100 further includes a cover 80, the cover 80 includes at least one second connecting column (not shown), the second connecting column is received in the receiving hole, to connect the housing 60 with the cover 80.

In at least one embodiment, the clamping portion 64 are protruded from the first connecting column 67.

In at least one embodiment, the clamping portion 64 is a clamping plate protruded from the first connecting column 67.

In at least one embodiment, the connecting element 70 further includes a first connecting plate 73 and a second connecting plate 74, the first connecting plate 73 and the second connecting plate 74 are arranged at two opposite sides of the connecting element 70. The first connecting plate 73 and the second connecting plate 74 both define a fourth through hole 731 communicated with the receiving groove 711 and the first through hole 63. The first connecting plate 73 is connected between an inner side of the housing 60 and a side of the receiving portion 71, the second connecting plate 74 is connected with another side of the receiving portion 71. At least one end of the first connecting plate 73 is extended out of the receiving portion 71, and acted as a side wall of the clamping groove 72 to clamp with the clamping portion 64. At least one end of the second connecting plate 74 is extended out of the receiving portion 71, and acted as a side wall of the clamping groove 72 to clamp with the clamping portion 64.

In at least one embodiment, the quantity of the receiving portion 71 is more than one, the receiving portions 71 can connected with each other or spaced apart from each other. When the receiving portions 71 are spaced apart from each other, the first connecting plate 73 and the second connecting plate 74 can connect two adjacent receiving portions 71 together.

The above description is merely some embodiments. It should be noted that for one with ordinary skills in the art, improvements can be made without departing from the concept of the present disclosure, but these improvements shall fall into the protection scope of the present disclosure.

What is claimed is:

1. A soil testing device, comprising: at least one sensor assembly, wherein, after the sensor assembly is inserted into soil, the sensor assembly and the soil cooperatively form a battery cell; and an analog meter, electrically connected with the at least one sensor assembly, wherein, when the analog meter is connected to the at least one sensor assembly, the sensor assembly is configured to transmit a micro current of the battery cell reflecting a measure of soil characteristic to the analog meter, and the analog meter is configured to display a value reflecting the soil characteristic;
wherein the soil testing device further comprises a housing, a switching assembly, and a connecting element; the switching assembly comprises a printed circuit board and connecting positions that are arranged on the printed circuit board and electrically connected to the analog meter;
the connecting element and the switching assembly are received inside the housing;
the housing is arranged with at least one clamping portion protruding from an inner wall of the housing;
the connecting element has at least one clamping groove and a top connecting plate; each of the at least one clamping portion is received in a respective one of the at least one clamping groove; the switching assembly is supported on the top connecting plate.

2. The soil testing device according to claim 1, further comprising: at least one sleeve, detachably sleeved on the at least one sensor assembly and configured to burnish the at least one sensor assembly.

3. The soil testing device according to claim 1, wherein the sensor assembly comprises: a sensor; and a sensor probe, connected with the sensor, wherein after the sensor is inserted into the soil, the sensor, the sensor probe, and the soil cooperatively form the battery cell.

4. The soil testing device according to claim 1, wherein the sensor assembly is a pH meter, a moisture meter, or a fertility meter.

5. The soil testing device according to claim 1, wherein the analog meter comprises: a first negative pole, electrically connected with the at least one sensor assembly.

6. The soil testing device according to claim 1, wherein the analog meter further comprises: a first positive pole; and
the connecting positions of the switching assembly comprise a first connecting position, arranged on the printed circuit board and electrically connected with the first positive pole.

7. The soil testing device according to claim 1, wherein the connecting positions of the switching assembly further comprise: at least one second connecting position, arranged on the printed circuit board and electrically connected with the at least one sensor assembly.

8. The soil testing device according to claim 1, further comprising: a photosensitive sensor, connected with the analog meter and the switching assembly, wherein the switching assembly is configured to electrically connect the analog meter with the photosensitive sensor, or configured to isolate the analog meter from the photosensitive sensor.

9. The soil testing device according to claim 8, wherein the photosensitive sensor comprises: a second positive pole, connected with the analog meter; and a second negative pole, connected with the switching assembly; and
the connecting positions of the switching assembly further comprise: a third connecting position, connected with the second negative pole of the photosensitive sensor.

10. The soil testing device according to claim 1, wherein the switching assembly further comprises: an actuating element, connected with the printed circuit board, wherein, the actuating element is configured to electrically connect the analog meter with the sensor assembly, or configured to isolate the analog meter from the sensor assembly.

11. The soil testing device according to claim 8, wherein the switching assembly further comprises: an actuating element, connected with the printed circuit board, wherein, the actuating element is configured to electrically connect the analog meter with the photosensitive sensor, or configured to isolate the analog meter from the photosensitive sensor.

12. The soil testing device according to claim 1, wherein the soil testing device further comprises: a housing, defining a window; and
the analog meter is received in the housing, and the analog meter further comprises: a dial, comprising at least one data range; and a pointer, movably arranged on the dial and configured to display the value reflecting the soil characteristic within the data range, the dial and pointer are at least partially exposed from the window.

13. The soil testing device according to claim 12, wherein the analog meter further comprises: a rotating element, connected with the pointer; a metal coil, wound around the rotating element, and electrically connected with the at least one sensor assembly; and a magnetic element, wherein, the metal coil is arranged in a magnetic field of the magnetic element, and after the metal coil is energized by the micro current, the metal coil is configured to drive the rotating element and the pointer to rotate under an action of a magnetic force of the magnetic element.

14. The soil testing device according to claim 1, wherein the soil testing device further comprises: a housing, defining a first through hole; and
the sensor probe defines: a second through hole, communicated with the first through hole, wherein, the first through hole and the second through hole are configured to receive an electric wire for electrically connect the at least one sensor assembly with the analog meter.

15. The soil testing device according to claim 14, further comprising: a connecting element, configured to connect the at least one sensor assembly with the housing.

16. The soil testing device according to claim 15, wherein the connecting element comprises: at lease one receiving groove, communicated with the first through hole and the second through hole, wherein the sensor assembly is received in the receiving groove and the first through hole.

17. The soil testing device according to claim 8, wherein the soil testing device further comprises: a housing, the housing defines a third through hole; and
the photosensitive sensor further comprises: a sensor body, received in the third through hole.

18. The soil testing device according to claim 1, wherein, the connecting positions of the switching assembly comprise: a first connecting position, at least one second connecting position, and a third connecting position;
the first connecting position is electrically connected with a positive pole of the analog meter;
each of the at least one second connecting position is further electrically connected with a respective one of the at least one sensor assembly; and
the third connecting position is further electrically connected with a photosensitive sensor, wherein the photosensitive sensor is configured to detect an ambient luminance level.

* * * * *